United States Patent [19]
Hara et al.

[11] Patent Number: 6,111,134
[45] Date of Patent: Aug. 29, 2000

[54] PROCESS FOR PRODUCING UNSATURATED GLYCOL DIESTER USING TELLURIUM AND RHODIUM CATALYST

[75] Inventors: Yoshinori Hara; Haruhiko Kusaka; Hironobu Ohno; Masami Okuda, all of Kanagawa, Japan

[73] Assignee: Mitsubishi Chemical Corporation, Tokyo, Japan

[21] Appl. No.: 09/158,115

[22] Filed: Sep. 22, 1998

[30] Foreign Application Priority Data

Sep. 25, 1997 [JP] Japan .................................. 9-259509
Feb. 13, 1998 [JP] Japan .................................. 10-31316

[51] Int. Cl.[7] .................................................. C07C 69/34
[52] U.S. Cl. ........................................................ 560/201
[58] Field of Search ................................... 560/211, 212, 560/201

[56] References Cited

U.S. PATENT DOCUMENTS 3,922,300 11/1975 Onoda et al. .
4,121,039 10/1978 Parthasarathy et al. .
5,208,399 5/1993 Miyake et al. .
5,777,155 7/1998 Sato et al. .

OTHER PUBLICATIONS

Patent Abstracts of Japan, vol. 002, No. 081 (C–016), Jun. 28, 1978 & JP 53 037609 A (Mitsui Toatsu Chem Inc.) Apr. 6, 1978.
Patent Abstracts of Japan, vol. 001, No. 149 (C–031), Nov. 30, 1977 & JP 52 091817 A (Sumitomo Chem Co., Ltd.) Aug. 2, 1977.
Database WPI, Section ch, week 7712, Derwent Publications Ltd., London, GB, Class E15, AN 77–20834Y, XP002089369 & JP 52 017422 A (Mitsubishi Chem Ind Ltd) Feb. 9, 1977.

*Primary Examiner*—Gary Geist
*Assistant Examiner*—Robert W. Deemie
*Attorney, Agent, or Firm*—Kaensaka & Takeuchi

[57] ABSTRACT

A method for production of unsaturated glycol diester, such as 1,4-diacetoxy-2-butene, is formed of reacting conjugated diene with carboxylic acid and molecular oxygen in the presence of a solid catalyst in the liquid phase under pressure. The catalyst is formed of rhodium and tellurium, which are supported on an inorganic porous carrier. The catalyst is stable, and the unsaturated glycol diester is prepared in high conversion and selectivity.

14 Claims, 1 Drawing Sheet

PROCESS FOR PRODUCING UNSATURATED GLYCOL DIESTER USING TELLURIUM AND RHODIUM CATALYST

FIELD OF THE INVENTION

The present invention relates to a process for an advantageous industrial production of unsaturated glycol diester such as 1,4-diacetoxy-2-butene by using a solid catalyst comprising at least Rh (rhodium) and Te (tellurium) as its composition components. The solid catalyst comprises rhodium and tellurium which are alloyed in a high degree, and has high stability in a reaction in which conjugated diene reacts with carboxylic acid and molecular oxygen, and capability to produce unsaturated glycol diesters with high catalytic activity and selectivity.

DESCRIPTION OF PRIOR ART

Unsaturated glycol diesters, for example butenediol diesters such as 1,4-diacetoxy-2-butene are important intermediates for producing 1,4-butanediol which is a raw material of engineering plastics, elastomers, elastic fibers, synthetic leathers and the like. Also, butenediol diesters are raw materials for high performance solvent and elastic fiber, as well as important intermediates for producing tetrahydrofran which is a solvent with a low boiling point and an excellent dissolving property.

Various processes for producing the butenediol diesters have been proposed.

Among them, a process is especially well known in which butadiene reacts with acetic acid and molecular oxygen in the presence of a solid catalyst wherein palladium coexists with a second component selected from tellurium, selenium, sulfur, and the like to produce butenedioldiacetate. For example, a catalyst containing, as active components, at least one selected from palladium, tellurium, and selenium is described in JPA48-72090. A catalyst containing as active components atr east one-selected from paradium, antimony and bismuth and at least one selected from tellurium and selenium is described in JPA 48-96513. A catalyst containing, as active components, (a) palladium, (b) tellurium, and (c) one selected from a group consisting of tin, germanium, and lead is described in JPA 55-69540. A catalyst containing, as active components, palladium, ruthenium, and tellurium supported on active carbon is described in JPA 53-121716. A catalyst containing palladium as an active component and thorium as a promoting a gent is described in JPA 54-59218.

However, catalysts comprising palladium as its primary component as described in these patent applications have provided not a few problems for the effective industrial production of objective product due to their low activity and low selectivity to the 1,4-diacetoxy-2-butene, On the other hand, a catalyst system containing rhodium as its primary active component is also proposed. For example, a catalyst containing, as active components, rhodium and tellurium and/or selenium is described in JPA 52-139004. A catalyst containing, as active components, rhodium or rhodium and tellurium and/or selenium is described in JPA 53-37609, and a catalyst as the latter with molybdenum incorporated additionally is described in JPA 53-44502. Further, a catalyst combining at least one metal selected from rhodium, palladium, and platinum with sulfur is described in JPA 53-2414. A catalyst combining at least one metal selected from palladium, rhodium, and platinum with tellurium and/or sulfur is described in 108010. A catalyst using, as active components, rhodium, platinum, palladium, and tellurium in certain ratios is described in JPA 52-91817.

When using rhodium as an active component, it is required to enhance the catalytic effects because rhodium is an expensive metal, but satisfactory results have not been obtained by the catalysts disclosed in the patent applications in the above. Especially severe problem lies in that rhodium is more susceptible to oxidation by oxygen as compared with palladium, and rhodium dissolves during the reaction in the presence of oxygen whereby degrading the catalytic activity.

OBJECT AND SUMMARY OF THE INVENTION

Therefore, an object of the present invention is to solve problems of prior art publications mentioned above and to provide a stable catalyst which contains rhodium and tellurium and has good stability for catalytic activity, and the method for preparing thereof, for the production of unsaturated glycol diester by the reaction of conjugated diene with carboxylic acid and molecular oxygen with high activity and selectivity. A further object of the present invention is to provide reaction conditions which are required for obtaining reaction results with high selectivity, activity, and stability in the process using the catalyst as mentioned above for the advantageous industrial production of unsaturated glycol diester.

The inventors of the present invention have made an extensive study in order to develop an industrially utilizable catalyst with higher catalytic activity than conventional ones, and in order to establish a process for producing carboxylic acid diester of unsaturated glycol using the aforementioned catalyst. Consequently, it has been found that, in the reaction in which conjugated diene reacts with carboxylic acid and molecular oxygen to produce unsaturated glycol diester, the stability of the catalyst containing Rh—Te as the main active component greatly depends on the degree of interaction between Rh and Te, i.e., the degree of alloying, so the higher the degree of alloying the higher the stability of catalyst during the reaction.

Further, it has been found that, when using the aforementioned catalyst in the production of carboxylic acid diester by the reaction of conjugated diene with corresponding carboxylic acid and molecular oxygen, the activity of the catalyst is higher and its stability is considerably improved as compared with the conventional reaction condition when oxygen coexists with conjugated diene in the reaction system under a special condition.

Moreover, the inventors have found that, in the catalyst which is prepared by supporting solid catalyst components comprising rhodium compound and tellurium compound on an inorganic porous carrier followed by drying and optional calcination and subsequent reduction treatment, a catalyst with higher catalytic activity and considerably improved stability as compared with the conventional catalysts can be obtained if the reducing gas is introduced in the reduction treatment under a special condition, and thus completed the present invention.

A first aspect of the invention is in a solid catalyst containing rhodium and tellurium as composition component, wherein the coordination number ratio (Rh—Te/Rh—Rh) of the of Rh atoms obtained in measurements of the extended X-ray absorption fine structure (hereafter indicated as XEAFS) of the Rh—K edge is in a range between 50/50 and 99/1.

A second aspect of the invention is in the method for producing unsaturated glycol diester by the reaction of conjugated diene with corresponding carboxylic acid and molecular oxygen under liquid pressure, in the presence of the solid catalyst containing rhodium and tellurium according to the said first aspect.

A third aspect of the invention is in the method for preparing the solid catalyst containing rhodium and tellurium described in the said first aspect, wherein it is prepared by loading rhodium compound and tellurium compound on an inorganic porous carrier to obtain supported catalyst; followed by heating the catalyst to a temperature higher than 70° C. in an inert atmosphere; and finally by subjecting the heated catalyst to a reduction treatment by introducing reducing gas while maintaining a temperature of 70° C. or more.

DESCRIPTION OF PREFERRED EMBODIMENTS

Figure 1:
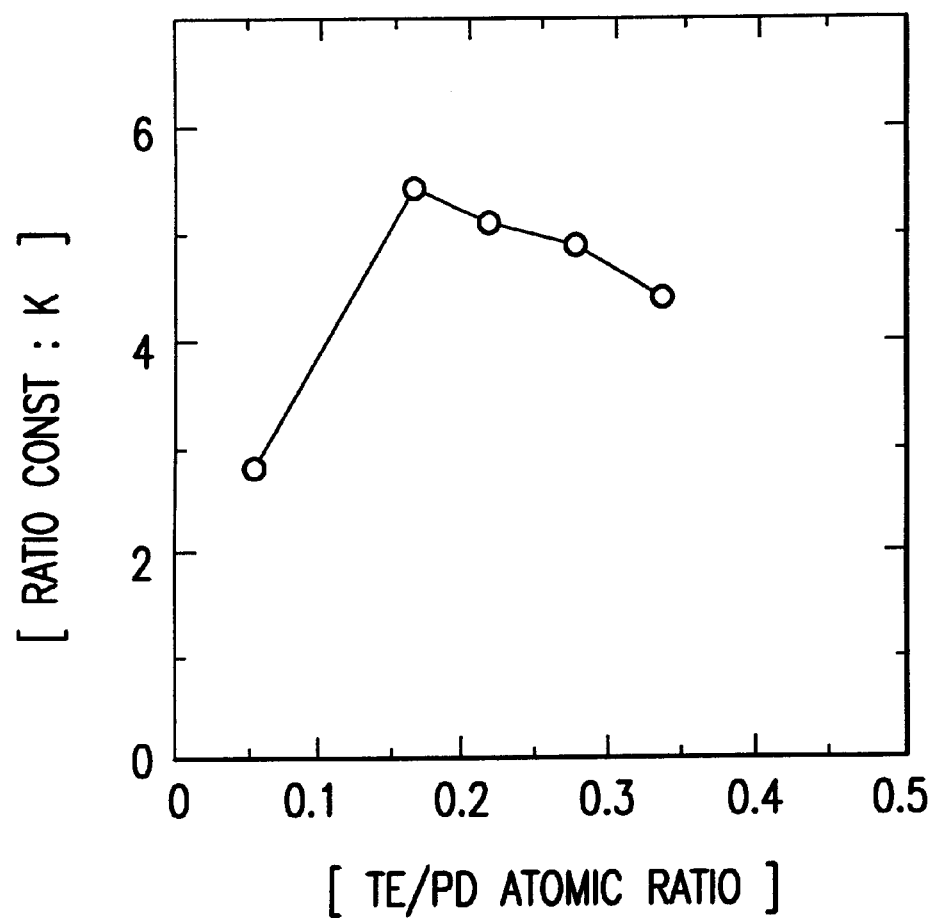
FIG. 1 is a graph in which Te/Rh atomic ratio is plotted against reaction rate constant, according to the reference example of the invention.

Hereinafter, embodiments of the present invention will be described in detail.

I. The solid catalyst containing rhodium and tellurium according to the invention The catalyst of the invention is a solid catalyst containing at least rhodium and tellurium as composition component and is specified by the coordination numbers of Rh atoms as obtained in measurements of the extended X-ray absorption fine structure (hereafter indicated as EXAFS). For particulars, it is a solid catalyst having a coordination number ratio (Rh—Te/Rh—Rh) of Rh atoms in a range between 50/50 and 99/1 as obtained in the EXAFS measurements at K edge of Rh atom.

EXAFS is a widely used method for analyzing the peripheral structure of a particular atom. It is especially effective means for knowing the degree of alloying in an alloy system containing plurality of metals by analyzing the numbers and kinds of atoms coordinating in the periphery of a particular atom in question. Thus, by the EXAFS measurements at Rh—K edge of a solid catalyst containing Rh and Te as its component, the structural characteristics of the periphery of Rh atom in this catalyst can be evaluated.

In the present invention, the degree of alloying is evaluated by the state of bond in the periphery of Rh atom. The state of bond is in turn evaluated by first measuring the X-ray absorption fine structure (XAFS) of K absorption edge of Rh atom, and then analyzing the extended X-ray absorption fine structure (EXAFS) included in the measurement. For details, the coordination number of the X-ray scattering atoms to the X-ray absorbing atom is observed and from the ratio of the coordination numbers, the bond state of Rh atom is determined and evaluated. Additionally, the basic theory and analysis method of the XAFS analysis is described in books such as, "Japanese Society of Spectroscopy, Measurements Series No.26 X-ray Absorption Fine Structure edited by Yasuo Utagawa".

The catalyst of the invention containing Rh and Te has a coordination number ratio in a range between 50/50 and 99/1 and more preferably, between 60/40 and 95/5. The coordination number ratio means, when noticing one Rh atom, the ratio of the number of Rh atoms existing nearest to the Rh atom to the number of Te atoms existing nearest to the Rh atom (The ratio will be called hereafter "coordination number ratio Rh—Te/Rh—Rh"). It indicates that the peripheral structure of Rh atom has more Te atoms than this lower limit value. In other words, the catalyst of the invention has higher degree of alloying between Rh and Te than this level.

The said coordination number ratio (Rh—Te/Rh—Rh) can be otherwise expressed with the atomic distance between the nearest Rh—Rh atoms, that is, as for one Rh atom, the distance from the Rh atom to another Rh atom in the nearest position (hereafter called "nearest Rh—Rh atomic distance). The metal crystal of pure Rh takes the face-centered cubic (fcc) structure, and it is known that the nearest Rh—Rh bond length is 2.68A. Meanwhile, when Rh and Te make alloy, the fcc structure is disturbed and the nearest Rh—Rh atomic distance changes. Generally, it is known that in Rh—Te alloy system, the nearest Rh—Rh atomic distance is longer than 2.68A. The nearest Rh—Rh atomic distance which satisfies the aforementioned coordination number ratio of the present invention is in the range between 2.74Å and 3.00Å, and preferably in the range between 2.75Å and 2.98Å.

Also, the catalyst of the present invention with a high degree of alloying is prepared with an atomic ratio (Te/M) of Te to a 8th group metal M (selected from Rh, Pt and Pd) of over 0.45, preferably 0.45–1.4, more preferably 0.45–1.0, further more preferably 0.55–0.9, and particularly 0.55–0.8 as will be described in the following explanation on the preparation method.

According to the present invention, a catalyst having a coordination number ratio of Rh atom (Rh—Te/Rh—Rh) in a range between 50/50 and 99/1 and, preferably, having a nearest Rh—Rh atomic distance of 2.74–3.00Å has high degree of alloying, good reaction stability and capability of producing unsaturated glycol diester with high catalytic activity, and high selectivity.

The Rh—Te catalysts which have been proposed in the aforementioned patent applications are prepared in Te/M atomic ratios of 0.4 or lower. However, it has been known from the studies by the inventors of the present invention that a catalyst having characteristics of the present invention can not be produced as long as such conventional Te/M atomic ratios and ordinary preparation processes are adapted. And, as the result of the further study, it has been known that a catalyst having aforementioned characteristics of the present invention can be prepared by increasing the Te component so that the Te/M atomic ratio is 0.45 or more, preferably 0.5 or more, more preferably 0.55 or more.

II. Method for preparing solid catalyst containing rhodium and tellurium of the present invention The catalyst of the present invention contains at least Rh and Te as effective components. The form of catalyst can be an alloy of Rh and Te, but it is more preferable that the catalyst comprising at least Rh and Te is supported on a carrier. In the case of supported form catalyst, the catalyst is generally prepared by first dissolving rhodium compound and tellurium compound and optionally, further compounds containing further metal elements, in a suitable solvent able to dissolve them; followed by applying the solution on a carrier material so that the said compounds are supported on the carrier; followed by drying and optionally calcinating the application product; and then subjecting the dried product to reduction treatment. In this case, there is no particular limitation in the method in which active components are supported on a carrier, and impregnation, immersion, precipitation, pore filling, and other methods can be used. In the following, a preparation method of supported type catalyst using the impregnation method is described as an example, but the present invention is by no means limited to the described method.

As for the physical characteristics of the carrier of the Rh—Te catalyst used in the reaction to produce carboxylic acid diester of unsaturated glycol, it is required that it is a porous material. The average pore diameter is particularly important and the preferable average pore diameter is over 3 nm, more preferably 5–50 nm. The definite reason for this is not yet clear, but the conceivable factors are for example; that the reaction substrate i.e. conjugated diene and reaction agent i.e. acetic acid and oxygen, are hindered to diffuse into the pore; and that the polymerization reaction is promoted because polymerizable conjugated diene molecules come comparatively close to each other. Also, a large total pore volume is preferable in terms of supported quantity, but too large pore volume is not preferable because it can decrease the strength. The preferable pore volume is in the range between 0.5 and 2.0 mL/g, and particularly between 0.7 and 1.5 mL/g.

Examples of such porous carriers used in the invention include carbon carriers such as activated carbon and graphite, and metal oxide carriers such as silica, alumina, titania, zirconia, and mixtures of these oxides. Among them, silica is used particularly favorably because the catalyst based on it shows good activity and selectivity in a reaction in which conjugated diene reacts with corresponding carboxylic acid and molecular oxygen to produce carboxylic diester of unsaturated glycol, as well as excellent physical strength, making the catalyst advantageous for the industrial use.

The examples of rhodium compounds and tellurium compounds used in the preparation of the catalyst of the invention include salts of inorganic acids such as nitric acid, sulfuric acid and hydrochloric acid, salts of organic acids such as acetic acid, hydroxides, and oxides. Also, complex salts, carbonyl complexes, and organic metal compounds represented by acetylacetonate salts are included.

For particulars, as rhodium compounds: rhodium chloride, rhodium nitrate, rhodium sulfate, rhodium acetate, rhodium hydroxide, rhodium oxide, hexachlororhodiumsodium, hexachlororhodiumammonium, chloropentamminerhodium, chlorohexamminerhodium, hexacyanorhodiumpotassium, trichlorotripyridinerhodium, chlorocyclooctadienilrhodium, tetrarhodiumdodecacarbonil and rhodium dicarbonilacetylacetonate can be exemplified.

Examples of tellurium compounds include tellurium chloride (11), (IV), tellurium oxide (IV), (VI), telluric acid ($H_6TeO_6$), sodium hydrodienetelluride (NaHTe), and diphenylditelluride ($PhTe)_2$. Also, tellurium metal can be used as the starting material for tellurium. Among the above, tellurium metal and telluric acid are preferable in terms of ease of handling and economy.

There is no limitation in the solvent to dissolve aforementioned rhodium compounds and tellurium compounds, and basically any solvents which can dissolve these metallic compounds may be used. When the metallic compound is a metallic organic compound, the solvents which can dissolve such compound are often organic solvents. However, when using the compounds dissolvable in aqueous solvent, water (even when containing acid or alkali) is preferred as solvent to organic solvents, in terms of safety and economy.

Regarding the process in which carrier material is immersed with catalyst component solution, a co-supporting process can be used in which carrier is immersed with the solution containing both rhodium compound and tellurium compound. Otherwise, the carrier can be first immersed with the solution of rhodium compound, dried, and then immersed with the tellurium compound with the subsequent drying. The sequence can be reversed.

As previously described, the present invention defines the optimum alloying state of the solid catalyst and it is preferable that the catalyst structure prepared by the above-described co-supporting process satisfies the definition of the invention. At least one additional catalyst component can be added to be supported after the co-supporting process is completed.

The required quantity of rhodium compound and tellurium compound, and optionally further compound of further metal element supported on the carrier can be supported in one time, or can be supported in several separate times. However, when supporting in several separate times, the drying process and optional calcination, and reduction treatment should be carried out after each supporting process.

The catalyst of the present invention comprises rhodium and tellurium as active components. However, optionally further elements such as the 8th group metals including Pt and Pd, and such as Au, Sb, Sn can be comprised additionally.

Regarding the quantity of rhodium supported on the carrier, the more the quantity, the higher the reaction activity per unit weight of the catalyst, but too much quantity is not preferable in terms of economy. In considering all factors the quantity of rhodium supported on the carrier is preferably selected from a range between 0.01 and 20% by weight, and more preferably between 0.1 and 10% by weight.

In the prior art, the quantity of tellurium supported on the carrier has been selected so that the atomic ratio (Te/M) is lower than 0.4, where Te indicates the number of Te atoms and M indicates the total number of at least one 8th group metal atom selected from Rh, pt. and Pd. This ratio has been selected only according to the optimum range in the prior Pd—Te system, and it is not necessarily optimum for the Rh— Te system. Especially important is that too small quantity of tellurium tends to lower the previously mentioned coordination number ratio (Rh—Te/Rh—Rh) as measured in the EXAFS measurement of Rh—K edge. Accordingly, a certain quantity of Te is required. On the other hand, too much quantity of tellurium is not preferable as it hinders the reaction and lowers the selectivity. In order to prepare the catalyst of the invention, the atomic ratio Te/M is selected from a range between 0.45 and 1.4, and preferably between 0.45 and 1.0. More particularly, in terms of maintaining the catalytic activity under the industrial conditions, a range between 0.55 and 0.9, and especially between 0.55 and 0.8 is preferable.

After the carrier is immersed with the solution of rhodium and/or tellurium compounds, the carrier is recovered from the solution and subsequently dried to remove the solvent from the catalyst system. As the drying method is used in this stage, either of the following methods; circulating dry gas through the fixed bed under heating, heating without gas circulation, or drying under reduced pressure, can be used.

In the case of drying by gas circulation through fixed bed under heating, the kind of the gas used is, for example, nitrogen, oxygen, argon, or any mixture of them. When using the gas mixture, its composition is arbitrary as far as it is in the industrial safety range. The flow rate of gas used is usually selected from a range of over 5 L/L·hr, preferably 10–10000 L/L·hr, and more preferably 20–5000 L/L·hr, as expressed in the space velocity (SV) to the catalyst. If the SV value is too low, the drying time becomes too long, and if it is too high, the cost becomes too high because of gas consumption. The drying temperature is selected from a range between 40 and 150° C., and more preferably, between 60 and 120° C. The drying time is usually 0.5–50 hours, and preferably 1–20 hours.

When the drying is carried out under reduced pressure, vacuum used can be basically any pressure under atmospheric, but in order to obtain a practical drying rate, vacuum of below 100 torr, and more preferably below 50 torr is used. Regarding the temperature used in the reduced pressure drying, basically, the ambient temperature gives sufficiently high drying rate, but heating can be used in order to increase the drying rate. The temperature range used in this case is between ambient temperature and 300° C., and preferably, between 50 and 200° C.

After the drying process, the obtained catalyst is optionally calcined by the following methods; heating under the hot gas circulation through the fixed bed, heating without the gas circulation, or the like. In the case of using the hot gas circulation, the kind of the gas used is, for example, nitrogen, oxygen, argon, or any mixture of them. When using the gas mixture, its composition is arbitrary as far as it is in the industrial safety range. The flow rate of gas used is usually selected from a range of over 5 L/L·hr, preferably 10–10000 L/L·hr, more preferably 20–5000 L/L·hr, as expressed in the space velocity (SV) to the catalyst. The calcining temperature is usually in the range between 150 and 800° C., and more preferably, between 300 and 700° C. The calcining time is preferably 1–20 hours.

Thus obtained dried and optionally calcined catalyst is then activated by the reduction treatment. As for the method of reduction treatment, either gas phase reduction or liquid phase reduction can be used. In the liquid phase reduction, any of the ordinary reducing agent such as hydrazine, sodium borohydride ($NaBH_4$), formic acid, and formalin can be used. In the gas phase reduction, reducing gas is used.

As the reducing gas used in the gas phase reduction, methanol, carbon monoxide, nitrogen monoxide and others, or gas mixture in which these gases are diluted with inert gas such as nitrogen, argon and helium can be used, but hydrogen is particularly preferable as the reducing gas because of its low toxicity. The preferable flow rate of reducing gas is 5–2000 L/L·hr, and more particularly 100–1500 L/L·hr, as expressed in the space velocity (SV) to the catalyst. The temperature in the gas phase reduction is selected from a range between 100 and 600° C., and more preferably, 150–500° C. The reduction treatment preferably lasts for 0.5–50 hours, and more preferably, it is selected from a range between 1 and 20 hours.

In the present invention, the catalyst is first heated to a temperature of over 70° C. before the reduction treatment begins. Then, the reducing gas is introduced and the reduction treatment is conducted at a predetermined temperature. The catalyst obtained in this manner is preferable as it has a high activity and a stability, which is considerably improved as compared with the conventional catalyst. The reason why the improved stability is obtained by using the above-described method of reduction is not yet made clear, but it is inferred, for example, that the alloying of rhodium and tellurium is promoted and thus, an ideal form of alloy in a catalyst is realized.

The heating temperature in the inert gas is selected so that the temperature at the introduction of reducing gas is 70° C. or more and particularly 100° C. or more. However, too high temperature may bring about calcination of active components. Therefore, the preferred temperature is 600° C. or less, and particularly, 500° C. or less.

III. Method for producing unsaturated glycol diester

By using the catalyst prepared according to the invention as described in the above, the reaction to produce unsaturated glycol diester is performed as described in the following.

Butadiene is typical as the conjugated diene which is one of the raw material of the reaction. Besides this, alkyl-substituted butadienes such as isoprene, 2,3-dimethylbutadiene and piperilene, and cyclic diene such as cyclopentadiene can be used. The raw material of the conjugated diene need not be pure and they can contain, for example, inert gas such as nitrogen, saturated hydrocarbon such as methane, ethane, butane or unsaturated hydrocarbon such as butene.

As the carboxylic acid which is another raw material of the reaction, lower aliphatic monocarboxilic acids such as, for example, formic acid, acetic acid, propyonic acid, and butyric acid can be used. Among them, acetic acid is particularly preferable because of its good reactivity and low cost. The quantity of the carboxylic acid is selected from a range between 1 and 60 mole %, and more preferably 3 and 30 mole % based on one mole of the conjugated diene.

The aforementioned carboxylic acids are reaction agents, but they can also serve as the solvents. Otherwise, special organic solvents inert to the reaction can be employed. Saturated hydrocarbons and esters can be used as the solvent.

As the molecular oxygen used in the method of the invention, usually a gas mixture, for example air, in which oxygen is diluted with inert gas such as nitrogen, is used because pure oxygen is not preferable for safety reasons. The quantity of oxygen used has no special limitation as far as it surpasses the reaction equivalent. However, it is required that the $O_2$ partial pressure in the reaction system according to the invention is kept under 10 $kgf/cm^2$. This requisite relates to the safety factor and the dissolving out of Rh. Namely, when the $O_2$ partial pressure in the reaction system is high, Rh becomes susceptible to oxidation, leading to its dissolving out. The favorably used $O_2$ partial pressure range is from 0.2 to 10 $kgf/cm^2$, and more preferably, from 1 to 8 $kgf/cm^2$.

In addition, the oxygen quantity also depends on the quantity of conjugated diene which is supplied simultaneously with oxygen. Namely, according to the reaction conditions of the invention, it is required that the molar fraction ratio ($xO_2/xDE$) between $O_2$ and conjugated diene (DE) existing in the liquid phase of the reaction system is kept under 0.5. Preferably, the molar fraction ratio ($xO_2/xDE$) is kept in a range between 0.005 and 0.2 during the reaction, and more preferably in a range between 0.01 and 0.15. With this condition, it can be avoided that the active points on the catalyst are subjected to more than necessary influence of $O_2$, resulting in the irreversible oxidation and loss of activity.

In further addition, in the present invention, if the reaction is carried out under the condition that the molar fraction of oxygen ($O_2$) existing in the liquid phase of the reaction system is kept 0.0002 or more, and preferably in a range between 0.0005 and 0.005, reaction activity is favorably enhanced.

The reason why the reaction conditions according to the present invention give reaction results with high activity and high stability has not yet been fully explained, but basically, the object of the reaction conditions claimed in the invention is in the control of oxidation-reduction properties of Rh, aiming to alleviate the load of Rh as little as possible. Rh is essentially more susceptible to oxidation than Pd. (The standard electrode potentials (EO) are, according to "Chemistry handbook 3rd revised edition", $Pd^{2+}+2e=Pd$; 0.915V whereas $Rh^{3+}+3e=Rh$, 0.758V.) Therefore, in a catalyst system including Rh, there should arise different restraints in the reaction conditions, from the Pd-based catalyst system.

Firstly, the inventors of the present invention have found that, in a catalyst system comprising Rh the $O_2$ partial pressure in the reaction system should be kept lower than a certain level. The inventors have found that, in the aforementioned manner, it is possible to prevent the dissolving out of Rh into the reaction liquid caused by oxidation of Rh. The inventors have further found that the ratio of $O_2$ and DE present in the liquid phase reaction system is an important factor. It is thought that this is because Rh is exposed to more than necessary $O_2$ attack when the quantity of DE is not sufficient, and an irreversible oxidation of Rh occurs, resulting in the decrease of catalytic activity with the lapse of reaction time. Thus, in order to maintain the stability of the Rh species relating to the reaction, it has become clear that the existence of DE over a certain quantity level in relation to the $O_2$ quantity present in the reaction system is necessary. From these results it is now evident that when using the Rh-based catalyst system, to apply the reaction conditions claimed in the present invention is extremely important.

The molar fractions of $O_2$ and conjugated diene in the liquid phase in the invention, $xO_2$ and $xDE$, were calculated according to the following equations.

$$Ki = (yi/xi) = \gamma i P0i/\pi$$

yi: molar fraction of i component in gas phase
xi: molar fraction of i component in liquid phase
γi: activity coefficient of i component
P0i : vapor pressure of i component
π: total pressure $$mi = (V \cdot yi + L \cdot xi)/(V \cdot L)$$

mi: total molar fraction of i component in both gas and liquid phases
V: total number of moles of all components in the gas phase
L: total number of moles of all components in the liquid phase $$xi = mi/(G(Ki-1)+1)$$

$$G = V/(V+L)$$

The "G" value was obtained by the convergence calculation so that $\Sigma xi = 1$ in the above equation, and based on this constant, the molar fraction of i component in the liquid phase xi was obtained. In addition, 1 was employed for activity coefficient; the vapor pressure of each component was obtained according to Antoine's equation; For Antoine's constant, a value taken from the literature (Lange Handbook of Chemistry) was employed. For particulars, the values in the following were employed.

Antoine's equation: $\log(P/mmHg) = A - B/(C + (t/^\circ C.))$

Antoine's constant (mmHg, ° C.)

|  | A | B | C |
|---|---|---|---|
| Oxygen | 6.98983 | 370.757 | 273.2 |
| Nitrogen | 6.86606 | 308.365 | 273.2 |
| 1,3-butadiene | 6.85941 | 935.531 | 239.554 |
| Acetic acid | 7.18807 | 1416.7 | 211.0 |

The reaction of the present invention in which conjugated diene reacts with carboxylic acid and molecular oxygen to produce the corresponding carboxylic acid diester of unsaturated glycol can be performed in either batch or continuous process. Regarding the form of usage of the catalyst, either fixed bed, fluidized bed, suspended tank, or other forms can be optionally employed.

Regarding the reaction temperature, the reaction is performed at a temperature over 20° C., but considering the reaction rate and by-product generation, the preferable reaction range is between 50 and 120° C.

The reaction is performed under overatmospheric pressure in order to raise the reaction rate. The preferable reaction pressure is selected from a range between 2 and 150 atm.

After the reaction is over the objective product, unsaturated glycol diester, is separated from reaction system with ordinary separation means such as distillation, and recovered unreacted conjugated diene and carboxylic acid are recycled to the reaction system to be reused.

DESCRIPTION OF EXAMPLES

The present invention will be described in more detail in the following with reference to the examples and comparative examples, but it is to be understood that the present invention is not limited to these specific examples, as far as it does not depart from its scope or spirit.

It should be noted that in the following, "%" indicates "% by weight".

The XAFS spectra of the catalyst prepared in the examples and comparative examples were measured and analyzed as follows.

i) XAFS spectrum measurement

The spectrum measurement was carried out by means of the Beamline 10B XAFS measuring apparatus of the High Energy Accelerator Research Institute Material Structure Science Laboratory Radiation Research Facility. The measurements were made by means of transmission mode. A channel-cut Si (311) was used for the crystal monochromator. The intensity I0 of incident X-ray beam was measured using a 17 cm ion chamber filled with Ar gas. The intensity I of X-ray beam which transmitted the sample was measured using a 31 cm ion chamber filled with Kr gas. For the measurement of XAFS spectrum of rhodium at the K absorption edge, the sample of the prepared catalyst was immediately sealed in a cylindrical glass cell covered with Capton film without a chance of contacting air. The measurement was conducted at ambient temperature.

The measuring range, interval of measuring point and the integrating time for each measuring point were set as follows:

For θ range from 9.591897° to 9.403897°, at intervals of 0.002686° with integrating time of 1 second for each point (70 points measured).

For θ range from 9.403897° to 9.342864°, at intervals of 0.000407° with integrating time of 1 second for each point (150 points measured).

For θ range from 9.342864° to 9.183935°, at intervals of 0.000993° with integrating time of 4 seconds for each point (160 points measured).

For θ range from 9.183935° to 8.955468°, at intervals of 0.002285° with integrating time of 4 seconds for each point (101 points measured).

Where θ indicates the incident angle of X-ray to the crystal monochromator.

ii) Analysis of the XAFS data

The analysis of the data obtained in the above measurements were conducted as follows:

The energy correction for the XAFS spectrum of rhodium at the K absorption edge was conducted so that the K absorption edge energy E0 of rhodium metal becomes 23220.7 eV, where E0 indicates the energy value in which first order differential coefficient becomes maximum in the spectrum range around the X-ray absorption edge (incident X-ray energy is from 23170 to 23320 eV).

Firstly, in order to eliminate the influence of the absorption other than that of rhodium, the background was subtracted ftom the raw spectrum. The background was determined by the McMaster's equation (AE−2.75 +B where A, B is arbitrary constant ) fitted to the raw spectrum in a range from 22725 eV to 23150 eV.

The absorption edge energy E0 of each sample was set at 23220.7 eV which is the same as the K edge energy E0 of rhodium metal. The base line p0(k) was determined by smoothing the spectrum $\mu(k)$ after the back-round subtraction in a range from 23240 eV to 24320 eV using the cubic spline method. EXAFS function $\chi(k)$ was obtained according to the equation $(\mu(k)-\mu0(k)/\mu0(E0)$, where $\mu0(E0)$ is value of the baseline $\mu0$ at the absorption edge energy E0 and k is the momentum of photoelectron defined by 0.5123% (E−0) ½. The unit of k is Å-1 and the unit of E is eV.

Then, the radial structure function F0(r) was obtained by Fourier transformation of the EXAFS function $k3\chi(k)$ weighted by k3, in the k range of from 3.5 Å-1 to 15.0 Å-1. The Hanning's function was used for the window function, and the window width Δk was set at 0.5 A-1.

Finally, the kind of the atom adjacent to rhodium atom, the bond distance between rhodium atom and the adjacent atom, and the coordination numbers of rhodium and the adjacent atom were obtained by the nonlinear least squares calculation (hereafter, referred to as "R space curve-fitting") so that the difference between the obtained radial structure function F0(r) and the calculated value Fc(r) obtained by Fourier transformation of the basic EXAFS formula becomes minimum. The range of Fourier transformation in the calculation of Fc(r) was from 3.5 Å-1 to 15.0 Å-1 for k, the same as in the F0(r) calculation, and the calculation range of the R space curve fitting was from 1.62 Å to 2.98 Å for r. The final results of coordination number was corrected by dividing the calculated value from the R space curve fitting with correction factor S0, so that the coordination number for Rh metal becomes 12, where S0 is obtained by the following equation.

S0 =(calculated value of coordination number for Rh metal obtained from R space curve-fitting )/12

In addition, the parameters of back scattering amplitude and phase shift for Rh—Rh and Rh—Te used in the R space curve-fitting calculation were obtained by means of a EXAFS function simulation software (so-called "FEFF") version 5.4. The parameters, which were input in the calculations with FEFF, were; 0.0036 for SIG2, 3 for NLEG and 1 and 1.0 for IIOLE. The atomic space coordinates which were input was a polar coordinates with rhodium atom at the center, calculated using the crystallographic structure data taken from the Inorganic Compounds Crystal Structure Data Base (so-called "ICSD"). For the parameter calculation of Rh—Rh, the crystallographic structure data of Rh metal (ICSD cord : 746284) was used, and for the parameter calculation of Rh—Te, that of Rh3Te2 alloy (ICSD cord: 14382) was used, respectively.

The evaluation method of the stability of catalytic activity in the 1,4-diacetoxy butene production for the catalysts prepared in the examples 1~7 and comparative examples 1–5 was as follows;

iii) Evaluation of stability of catalytic activity in 1,4-diacetoxy butene production Thus prepared catalyst of 4 g was packed in a stainless steel reaction tube with an inner diameter of 12 mm (effective cross sectional area 1.005 cm$^2$). Under a reaction pressure of 60kgf/cm$^2$ and a reaction temperature of 80° C., 0.15 mol/hour of 1,3-butadien, 2.5 mol/hour of acetic acid and 100 NL/h of nitrogen containing 6% of oxygen was passed through the tube and the reaction was performed continuously for 7 hours. Under the above reaction condition, the molar fraction of $O_2$, that is $xO_2$, was 0.003 and $xO_2$ /xDE was 0.72. The resultant liquid fraction of this reaction was subjected to gas chromatography for the quantitative determination of the reaction products.

The catalytic activity was indicated by the total generation quantity in mmol per kg of catalyst per hour, of 3,4-diacetoxybutene-1 (3,4-DABE), 3-hydroxy-4-acetoxybutene-1 (3,4-HABE), 1-acetoxycrotonaldehyde and 1,4-diacetoxybutene-2 (1,4-DABE) contained in the reaction product.

The selectivity of 1,4-DABE or 3,4-DABE was obtained by the following equation.

$$\text{Selectivity} = \frac{\text{(generation quantity of 1,4-}DABE\text{ or 3,4-}DABE\text{)}}{\text{(Total generation quantity of 3,4-}DABE\text{, 3,4-}HABE\text{, 1,4-}DABE\text{)}} \times 100$$

The selectivity of monoacetoxy-1,3-butadiene (MABD) was indicated by the ratio of MABD in the total generated products.

The activity decrease ratio is indicated by a value which is obtained by dividing the activity corresponding to 1 hour from the 6th hour to 7th hour after the start of the reaction, by the activity corresponding to 1 hour from the 11st hour to the 2nd hour after the start of the reaction.

The dissolving ratio for Rh and Te was obtained by analyzing with ICP (Induced Coupled Plasma Emission Analysis) the reaction liquid after 7 hours of reaction for the content of each metal, and calculating from the analyzed values the quantity ratio of dissolved metals to the originally supported metals expressed in % by weight.

EXAMPLE 1

Preparation of a catalyst (3% Rh—Te/Sio$_2$, Te/Rh=0.5)

1.040 g of tellurium metal (made by NE Chemcat) was placed in a 50 ml volumetric flask. Then, 29.85 c of 35% aqueous solution of nitric acid was added to the flask to dissolve the tellurium metal. Then, 8.507 g of 19.94% aqueous solution of rhodium chloride (rhodium chloride made by NE Chemcat and dissolved in desalted water) was added and the solution was made up to 50 ml by adding additional desalted water, giving 59.06 g of solution. Then, 20.75 g of silica carrier beads (CARiACT-15:commercial name, made by Fuji Cilicia Chemical, particle diameter from 1.7 mm to 3.36 mm, hereafter called "CARiACT-15") was added to the solution and immersed for 1 hour at ambient temperature. After filtering and subsequent centrifuge treatment to remove the solution, 44.85 g of catalyst was obtained. This catalyst was placed in a Pyrex glass tube with an inner diameter of 2.5 cm (effective cross sectional area 4.9 cm$^2$). The catalyst was then maintained at 150° C. for 3 hours, then at 500° C. for additional 2 hours under the passing of air flow in a rate of 1.25 NL per minute. The catalyst was then cooled to ambient temperature. Then, the gas flow was switched to nitrogen, and the temperature was raised to 300° C. in 1 hour under the passing of gas flow in a rate of 0.63 NL per minute. At this temperature, the gas flow was switched to hydrogen, and the temperature was raised from 300° C. to 400° C. in 1 hour and was maintained at 400° C. for 2 hours under the passing of gas flow in a rate of 0.63 NL per minute. Then the gas flow was switched to nitrogen, and the system was cooled to ambient temperature. Thus, 21.87 g of activated catalyst was obtained. This catalyst contained 3.17% of rhodium and 1.94% of tellurium, Te/Rh atomic ratio being 0.495.

Thus prepared catalyst was analyzed and evaluated regarding the coordination number ratio Rh—Te/Rh—Rh, the nearest Rh—Rh atomic distance and the stability of catalytic activity in the 1,4-diacetoxybutene production, and the results are given in Table 1.

TABLE 1

|  | Comparative Example 1 | Comparative Example 2 | Comparative Example 3 | Example 1 | Example 2 |
|---|---|---|---|---|---|
| Te Source | Te(O) | Te(O) | Te(O) | Te(O) | Te(O) |
| Te/Rh atomic ratio | 0.3 | 0.3 | 0.4 | 0.5 | 0.7 |
| Support | activated carbon | $SiO_2$ | $SiO_2$ | $SiO_2$ | $SiO_2$ |
| EXAFS |  |  |  |  |  |
| coordination number ratio (Rh-Te/Rh—Rh) | 27/73 | 17/83 |  | 74/26 | 69/31 |
| Rh—Rh atomic distance (Å) | 2.69 | 2.70 |  | 2.76 | 2.81 |
| activity (mmol/kg-cat · h) |  |  |  |  |  |
| 1.5 h | 4643 | 8112 | 11014 | 10463 | 9860 |
| 6.5 h | 2670 | 6576 | 10792 | 10988 | 10128 |
| activity decrease (6.5 h/1.5 h) | 0.58 | 0.81 | 0.97 | 1.05 | 1.03 |
| selectivity (4.5 h) |  |  |  |  |  |
| 1,4-DABE | 91.7 | 93.6 | 95.7 | 96.5 | 97.1 |
| 3,4-DABE | 6.2 | 4.7 | 3.5 | 2.9 | 2.3 |
| MABD | 1.1 | 1.1 | 0.4 | 0.4 | 0.3 |
| metal dissolving ratio (wt %) |  |  |  |  |  |
| Rh | 5.7 | 12.3 | 7.5 | 7.2 | 5.7 |
| Te | 9.4 | 19.7 | 10.0 | 7.6 | 5.1 |

EXAMPLE 2

Preparation of a catalyst(3% Rh—Te/$SiO_2$, Te/Rh =0.7) 1.470 g of tellurium metal (made by NE Chemcat) was placed in a 50 ml volumetric flask. Then, 42.20 g of 35% aqueous solution of nitric acid was added to the flask to dissolve the tellurium metal. Then, 8.475 g of 19.94% aqueous solution of rhodium chloride (rhodium chloride made by NE Chemcat and dissolved in desalted water) was added and the solution was made up to 50 ml by adding desalted water, giving 61.42 g of solution. Then, 20.83 g of silica carrier beads (CARiACT-15) was added to the solution and immersed for 1 hour at ambient temperature. After filtering and subsequent centrifuge treatment to remove the solution, 46.05 g of catalyst was obtained. The obtained catalyst was dried, calcinated, and reduced in the same manner as in Example 1 to give 22.13 g of activated catalyst. This catalyst contained 3.14% of rhodium and 2.72% of tellurium, Te/Rh atomic ratio being 0.701.

Thus prepared catalyst was analyzed and evaluated regarding the coordination number ratio Rh—Te/Rh—Rh, the nearest Rh—Rh bond distance, and the stability of catalytic activity in the 1,4-diacetoxybutene production, and the results are given in Table 1.

COMPARATIVE EXAMPLE 1

Preparation of a catalyst (3% Rh—Te/AC, Te/Rh=0.3)

3% Rh—Te/AC (Te/Rh =0.3) catalyst was prepared in the same manner as described in Example 1 of JPA 52-139004. The activated carbon used therein was palm shell activated carbon (made by Tsurumi Coal Co., HC-16, surface area 1300 m²/g, pore volume 0.79 cc/g) according to the description of the above patent application.

Thus prepared catalyst was analyzed and evaluated regarding the coordination number ratio Rh—Te/Rh—Rh, the nearest Rh—Rb bond distance, and the stability of catalytic activity in the 1,4-diacetoxybutene production, and the results are given in Table 1.

COMPARATIVE EXAMPLE 2

Preparation of a catalyst (3% Rh—Te/$SiO_2$, Te/Rh 0.3)

1.238 g of tellurium metal (made by NE Chemcat) was placed in a 100 ml volumetric flask. Then, 42.20 g of 35% aqueous solution of nitric acid was added to the flask to dissolve the tellurium metal. Then, 21.693 g of 15.35% aqueous solution of rhodium chloride (rhodium chloride made by NE Chemcat and dissolved in desalted water) was added and the solution was made up to 100 ml by adding additional desalted water, giving 113.01 g of solution. Then, 45.64 g of silica carrier beads (CARiACT-15) was added to the solution and immersed for 1 hour at ambient temperature. After filtering and subsequent centrifuge treatment to remove the solution, 96.12 g of catalyst was obtained. Of this catalyst, 42.25 g was dried, calcinated, and reduced in the same manner as in Example 1 to give 20.97 g of activated catalyst. This catalyst contained 3.12% of rhodium and 1.16% of tellurium, Te/Rh atomic ratio being 0.300.

Thus prepared catalyst was analyzed and evaluated regarding the coordination number ratio Rh—Te/Rh—Rh, the nearest Rh—Rh bond distance, and the stability of catalytic activity in the 1,4-diacetoxybutene production, and the results are given in Table 1.

COMPARATIVE EXAMPLE 3

Preparation of a catalyst (3%Rh—Te/$SiO_2$, Te/Rh=0.4)

0.414 g of tellurium metal (made by NE Chemcat) was placed in a 25 ml volumetric flask. Then, 12.03 g of 35% aqueous solution of nitric acid was added to the flask to dissolve the tellurium metal. Then, 8.08 g of 10.33% aqueous solution of rhodium chloride (rhodium chloride made by NE Chemcat and dissolved in desalted water) was added and the solution was made up to 25 ml by adding additional desalted water, giving 28.95 g of solution. 17.78 g of silica carrier beads (CARiACT-15) was added to the solution and immersed for 1 hour at ambient temperature. After filtering and subsequent centrifuge treatment to remove the solution, 37.84 g of catalyst was obtained. The obtained catalyst was dried, calcinated, and reduced in the same manner as in Example 1 to give 19.59 g of activated catalyst. This catalyst contained 3.10% of rhodium and 1.54% of tellurium, Te/Rh atomic ratio being 0.40 1.

Thus prepared catalyst was analyzed and evaluated regarding the coordination number ratio Rh—Te/Rh—Rh, the nearest Rh—Rh bond distance and the stability of catalytic activity in the 1,4-diacetoxybutene production, and the results are given in Table 1.

In Comparative Example 3, EXAF has not yet been measured, but it is estimated that the coordination number ratio Rh—Te/Rh—Rh is around 40/60 and the nearest Rh—Rh bond distance is around 2.73 Å.

As is apparent from Table 1, the catalysts of the examples (catalysts of the invention) show high activity and high selectivity to the main product (1,4-DABE) while they show low selectivity to 3,4-DABE or MABD which are by-products. Also, they show high stability with little or no decrease in catalytic activity after the reaction time of 6.5 hours. Further, they show low dissolving ratio for Rh and Te. In contrast, the catalysts of the comparative examples show inferior activity and selectivity, severely decreased activity with the lapse of reaction time, and high dissolving ratio for the metals. It is a surprising fact that by using a catalyst with an ideal state of alloying, as shown in the examples of the invention, the dissolving ratio of Te is suppressed to a low level, in spite of the conventional expectation that the dissolving ratio of Te will increase with the increased Te/Rh ratio. The inventors of the invention, having noticed the importance of dissolving ratio of metals, especially that of Te, which have not utterly been referred to in the prior art, found that this dissolving ratio has correlation with the state of alloying of the catalyst, and have defined the optimum catalytic structure. A high dissolving ratio of metals not only gives unfavorable influence on the reaction activity, but also it causes various severe problems to the process such as clogging of pipes. Also in this respect, the present invention offers much industrial merits.

EXAMPLE 3

Preparation of a catalyst(3% Rh—Te/SiO$_2$, Te/Rh=0.5)

A catalyst (3% Rh—Te/SiO$_2$, Te/Rh =0.5) was prepared following the similar procedure as in Example 1, except that telluric acid (H$_6$TeO$_6$) was used instead of tellurium metal and that water was used instead of 35% aqueous solution of nitric acid. The evaluation results of the stability of catalytic activity in the 1,4-diacetoxybutene production using the obtained catalyst are shown in Table 2.

0.377 g of telluric acid (H$_6$TeO$_6$) was placed in a 25 ml volumetric flask and was dissolved in added water. The solution was made up to 25 ml by additional water giving 25.28 g of solution by weight. Into this solution, 18.10 g of the catalyst obtained in Example 2 was added and stood immersed for around 1 hour. After confirming that the solution has completely penetrated into the catalyst, the catalyst was centrifuged to remove the excessive solution. At this stage, the weight of the solution remaining in the pore was 17.51 g. From this weight, the quantity of Te additionally supported on the catalyst was calculated to be 0.20 as expressed in the atomic ratio Te/Rh. Then, the catalyst was placed in a quartz tube with an inner diameter of 30 mm, and was dried at 150° C. under the passing of air at a flow rate of 1.0 L/minute for 3 hours. From the dried catalyst, 9.02 g was taken and placed in a Pyrex tube with an inner diameter of 20 mm and the temperature was raised to 300° C. under passing of argon gas at a rate of 300 ML/minute. When the temperature reached 300° C., the gas supply was switched to hydrogen gas keeping the same flow rate, and the temperature was again raised to 400° C. The reduction treatment lasted for 2 hours at this temperature. Thus, 8.99 g of the reduced catalyst supporting additional Te was obtained.

The evaluation results of the stability of catalytic activity in the 1,4-diacetoxybutene production using the obtained catalyst are shown in Table 2.

As is apparent from Table 2, Comparative Example 4 shows a very low catalytic activity with substantial decrease in activity during the reaction, although the dissolving ratios of metals are low, making the catalyst almost unusable in the industrial conditions. This fact means that, in Comparative Example 4 in which the ratio Te/Rh is high, the metals do not form an optimum alloying state of the invention, but they form a Te-rich inactive catalytic phase.

REFERENCE EXAMPLE
(Reaction example of Te/Pd system)

TABLE 2

|  | Comparative Example 4 | Example 3 | Example 4 | Example 5 | Example 6 | Example 7 | Comparative Example 5 |
| --- | --- | --- | --- | --- | --- | --- | --- |
| Te Source | H$_6$TeO$_6$ | H$_6$TeO$_6$ | H$_6$TeO$_6$ | H$_6$TeO$_6$ | H$_6$TeO$_6$ | H$_6$TeO$_6$ | H$_6$TeO$_6$ |
| Te/Rh atomic ratio | 0.3 | 0.5 | 0.7 | 0.7 + 0.2 | 0.9 | 1.1 | 1.5 |
| Support | SiO$_2$ | SiO$_2$ | SiO$_2$ | SiO$_2$ | SiO$_2$ | SiO$_2$ | SiO$_2$ |
| activity (mmol/kg-cat · h) | | | | | | | |
| 1.5 h | 10046 | 11147 | 10525 | 6270 | 4075 | 3320 | 606 |
| 6.5 h | 7239 | 11147 | 10751 | 6304 | 2589 | 1439 | 237 |
| activity decrease ratio (6.5 h/1.5 h) | 0.72 | 1.00 | 1.02 | 1.01 | 0.64 | 0.43 | 0.39 |
| selectivity (4.5 h) | | | | | | | |
| 1,4-DABE | 93.9 | 96.0 | 96.6 | 96.4 | 88.64 | 78.7 | 70.1 |
| 3,4-DABE | 4.7 | 3.0 | 2.9 | 3.1 | 7.44 | 13.9 | 16.7 |
| MABD | 1.0 | 0.4 | 0.3 | 0.3 | 1.2 | 2.8 | 2.9 |
| metal dissolving ratio (wt %) | | | | | | | |
| Rh | 12.7 | 8.9 | 7.5 | 4.0 | 10.4 | 9.9 | 4.4 |
| Te | 19.2 | 8.8 | 6.8 | 6.3 | 8.2 | 7.4 | 6.7 |

EXAMPLES 4, 6, 7 AND COMPARATIVE EXAMPLE 4, 5

The Catalysts were prepared following the similar procedure as in Example 3, except that the atomic ratio Te/Rh was varied as shown in Table 2. The evaluation results of the stability of catalytic activity in the 1,4-diacetoxybutene production using the obtained catalyst are shown in Table 2.

EXAMPLE 5

Tellurium was additionally supported on the catalyst (Te/Rh=0.7) prepared in Example 2 following the procedure in the following;

A Te/Pd system catalyst was prepared as follows. Pd nitrate was used instead of Rh nitrate of Example 1, and the preparation procedure of the catalyst comprises: drying the catalyst with air flow at 150° C. for 3 hours; raising the temperature to 400° C. in 1 hour after switching air to hydrogen gas flow at a rate of 0.63 NL/min.; keeping this temperature for 2 hours; and cooling down in the nitrogen gas flow. Using thus obtained activated catalyst, the acetoxylation reaction was performed as in Example 1. The activity measurement results for varied Te/Pd ratios of 0.05, 0.16, 0.21, 0.27 and 0.33 are shown in FIG. 1. As seen from FIG.

1, in the case of Te/Pd system, the optimum Te/Pd atomic ratio showing the maximum reaction activity is at around 0.2, and over this point, the activity decreases as Te/Pd atomic ratio increases.

EXAMPLE 8

Acetoxylation reaction of butadiene 8 g of rhodium-tellurium catalyst obtained in Example 1 was packed in a SUS reaction tube with an inner diameter of 25 mm. The system was pressurized to 60 kgf/cm$^2$ with nitrogen gas, and under the passing of nitrogen gas and acetic acid, the temperature was raised to 80° C., the flow rate of acetic acid being 650 ml/h. Then, 1,3-butadiene started to be supplied at a rate of 675 mmol/h. 1 hour after the start of butadiene addition, the nitrogen gas was stopped and 6% $O_2/N_2$ started to be supplied at a rate of 433 Nl/h, and the reaction was carried out keeping the reaction pressure at 60 kgf/cm$^2$ (the oxygen partial pressure in the reaction system was 3.6 kgf /cm$_2$). In the course of reaction, sampling was made at 4–5 hours interval and the taken sample was subjected to gas-chromatography for the quantitative determination of the products. The results of activity and selectivity are shown in Table 3.

The evaluation of the catalytic activity was indicated by the total generation quantity in mmol of high boiling point products and medium boiling point products shown in the following, per 1 kg catalyst per hour (mmol products/(kg-catalyst·hr)).

medium boiling point products:
    3,4-diacetoxybutene (3,4-DABE)
    3-hydroxy-4-acetoxybutene (3,4-HABE)
    1-acetoxycrotonealdehyde
    1,4-diacetoxy-2-butene (1,4-DABE)
    1-hydoxy-4-actoxybutene
high boiling point products:
    1,4-dihydroxy-2
    diacetoxyoctatriene
    1,1,4-riacetoxybutene-2

The selectivity was indicated by the 1,4-DABE selectivity which is the ratio of 1,4-diacetoxy-2-butene (1,4-DABE) in the total generated products including said high and medium boiling point products plus low boiling point products which are shown below, expressed in mol %.

low boiling point products:
    furan
    acrolein
    monoacetoxybutene (MABE)
    butanol
    monoacetoxy-1,3-butadiene (MABD)

The dissolving ratio for Rh and Te was obtained by analyzing with IC P (induced Coupled Plasma Emission Analysis) the reaction liquid after 7 hours of reaction for the content of each metal, and calculating from the analyzed values the quantity ratio of dissolved metals to the originally supported metals expressed in % by weight. The results are shown in Table 3.

EXAMPLE 9

A catalyst was prepared in the same manner as in Example 8, except that the supply rate of butadiene was 337 mmol/h. The acetoxylation reaction was carried out in the same manner as in Example 8 to give the results shown in Table 3.

EXAMPLE 10

A catalyst was prepared in the same manner as in Example 8, except that the supply rate of butadiene was 169 mmol/h. The acetoxylation reaction was carried out in the same manner as in Example 8 to give the results shown in Table 3.

EXAMPLE 11

A catalyst was prepared in the same manner as in Example 8, except that the supply rate of butadiene was 84.3 mmol/h. The acetoxylation reaction was carried out in the same manner as in Example 8 to give the results shown in Table 3.

TABLE 3

| | molar fraction ratio | xO2 in liq. | Activity (mmol/ | 1,4-DABE selectivity | metal dissolving ratio (wt %) | |
|---|---|---|---|---|---|---|
| | xO$_2$/xBD | phase | kg-cat · h) | (mol %) | Rh | Te |
| Example 8 | 0.0720 | 0.0030 | 8870 | 97.1 | 4.3 | 3.1> |
| Example 9 | 0.1422 | 0.0031 | 8987 | 96.5 | 10.8 | 5.6 |
| Example 10 | 0.2816 | 0.0031 | 5230 | 95.9 | 16.1 | 9.6 |
| Example 11 | 0.5626 | 0.0031 | 2375 | 95.8 | 16.5 | 11.0 |

From Table 3 it is found that, under the conditions of the invention, the reaction can be carried out with low dissolving out of metals and with high activity and selectivity, making it possible to produce 1,4-DABE with high efficiency.

Apart from this, other series of experiments were carried out in which $O_2$ concentration was varied in the $O_2/N_2$ gas supplied to the reaction system. In these experiments it was made clear that the dissolving out of Rh increases with the increase of $O_2$ concentration from 3% to 6%, although reaction activity increases with it. From these results, it was known that the increase of $O_2$ concentration provides tendency to enhance Rh dissolving. Also, the increase of $O_2$ concentration is not preferable from the standpoint of safety, as it can bring the composition of reaction system into the explosion range. In conclusion, raising the $O_2$ concentration unnecessarily is not preferable from the standpoint of both Rh dissolving and safety.

It is also expected that, if the $O_2$ concentration in the reaction liquid phase is too low, the reaction activity will be too low.

As described in detail in the above, by using the catalyst of the present invention in the reaction in which conjugated diene reacts with carboxylic acid and molecular oxygen to produce unsaturated glycol diester, the objective product can be produced with high activity and selectivity, and with stability for a long span of reaction time. Especially, the knowledge that the dissolving ratio of the metals, above all Te, which was hardly noticed in the prior art, correlates with the alloying state of the catalyst, is obtained for the first time by the present invention. With this knowledge, it has been made possible to select the optimum catalyst structure used in the industrial acetoxylation reaction, bringing about a substantial merit to the industry.

We claim:

1. A method for production of unsaturated glycol diester, wherein conjugated diene reacts with carboxylic acid and molecular oxygen in a presence of a solid catalyst comprising rhodium and tellurium, in a liquid phase under pressure, said solid catalyst having a coordination number ratio of Rh—Te/Rh—Rh measured in an Extended X-ray Absorption Fine Structure measurement at an Rh—K edge in a range between 50/50 and 99/1.

2. A method for the production of unsaturated glycol diester as claimed in claim 1, wherein the reaction is carried out under the condition that the oxygen partial pressure in the reaction system is 10 kgf/cm$^2$ or less and that the molar fraction ratio (xO$_2$/xDE) between oxygen (O$_2$) and conjugated diene (DE) existing in the liquid phase of the reaction system is kept 0.5 or less.

3. A method for the production of unsaturated glycol diester as claimed in claim 1, wherein the reaction is carried out under the condition that the molar fraction ratio (xO$_2$/xDE) between oxygen (O$_2$) and conjugated diene (DE) existing in the liquid phase of the reaction system is kept 0.2 or less.

4. A method for the production of unsaturated glycol diester as claimed in claim 1, wherein the reaction is carried out under the condition that the molar fraction of oxygen (O$_2$) existing in the liquid phase of the reaction system is kept 0.0002 or more.

5. A method for the production of unsaturated glycol diester as claimed in claim 1, including: preparing a solid catalyst by supporting rhodium compound and tellurium compound on an inorganic porous carrier; heating to a temperature of 70° C. or more in the presence of inert gas; and reducing the catalyst by introducing reducing gas while maintaining a temperature of 70° C. or more.

6. A method for the production of unsaturated glycol diester as claimed in claim 5, wherein the temperature is in a range between 100 and 600° C.

7. A method for the production of unsaturated glycol diester as claimed in claim 5, wherein the reducing gas is hydrogen.

8. A method for the production of unsaturated glycol diester as claimed in claim 5, wherein the conjugated diene used for the reaction is butadiene.

9. A method for the production of unsaturated glycol diester as claimed in claim 5, wherein the carboxylic acid used for the reaction is acetic acid.

10. A method for production of unsaturated glycol diester, wherein conjugated diene reacts with carboxylic acid and molecular oxygen in a presence of a solid catalyst comprising rhodium and tellurium, in a liquid phase under pressure, said solid catalyst having a nearest Rh—Rh atomic distance measured in an Extended X-ray Absorption Fine Structure measurement at an Rh—K edge in a range between 2.74 Å and 3.00 Å.

11. A method for production of unsaturated glycol diester, wherein conjugated diene reacts with carboxylic acid and molecular oxygen in a presence of a solid catalyst, in a liquid phase under pressure, said solid catalyst comprising Rh and Te, wherein an atomic ratio between Te and Rh of Te/Rh in the solid catalyst is from 0.45 to 1.4.

12. A method for the production of unsaturated glycol diester as claimed in claim 11, wherein the solid catalyst consists essentially of rhodium and tellurium.

13. A method for the production of unsaturated glycol diester as claimed in claim 10, wherein the solid catalyst consists essentially of rhodium and tellurium.

14. A method for the production of unsaturated glycol diester as claimed in claim 11, wherein the solid catalyst consists essentially of rhodium and tellurium.

* * * * *